(12) United States Patent
Bowsher

(10) Patent No.: US 10,238,826 B2
(45) Date of Patent: Mar. 26, 2019

(54) RESPIRATORY MASK

(75) Inventor: Richard Francis Bowsher, Berkshire (GB)

(73) Assignee: Intersurgical AG, Vaduz (LI)

( * ) Notice: Subject to any disclaimer, the term of this patent is extended or adjusted under 35 U.S.C. 154(b) by 120 days.

(21) Appl. No.: 14/115,016

(22) PCT Filed: Mar. 27, 2012

(86) PCT No.: PCT/GB2012/050676
§ 371 (c)(1),
(2), (4) Date: Oct. 31, 2013

(87) PCT Pub. No.: WO2012/150441
PCT Pub. Date: Nov. 8, 2012

(65) Prior Publication Data
US 2014/0053845 A1 Feb. 27, 2014

(30) Foreign Application Priority Data
May 3, 2011 (GB) .................... 1107314.5

(51) Int. Cl.
*A61M 16/00* (2006.01)
*A61M 16/06* (2006.01)
A62B 18/08 (2006.01)

(52) U.S. Cl.
CPC ........ *A61M 16/06* (2013.01); *A61M 16/0616* (2014.02); *A61M 2205/0216* (2013.01); *A62B 18/08* (2013.01)

(58) Field of Classification Search
CPC .............................. A61M 16/06; A61M 15/00
See application file for complete search history.

(56) References Cited

U.S. PATENT DOCUMENTS

| 4,167,185 A | 9/1979 | Lewis |
| 4,226,234 A | 10/1980 | Gunderson |

(Continued)

FOREIGN PATENT DOCUMENTS

| EP | 0196204 A2 | 3/1986 |
| EP | 0196204 A2 | 10/1986 |

(Continued)

OTHER PUBLICATIONS

PCT International Search Report for corresponding PCT Patent Application No. PCT/GB2012/050676, dated Jul. 5, 2012 (4 pages).

(Continued)

*Primary Examiner* — Gregory Anderson
*Assistant Examiner* — Victoria Murphy
(74) *Attorney, Agent, or Firm* — LeClairRyan PLLC

(57) ABSTRACT

This invention relates to a respiratory mask for delivering an inhalation fluid to the airways of a wearer. The respiratory mask includes a body of generally concave shape and having a peripheral edge, the body being adapted to provide a cavity in use about the mouth and nose of a wearer such that the inhalation fluid can be inhaled by the wearer from the cavity. The respiratory mask includes a resilient seal formation depending from at least a portion of the peripheral edge. The resilient seal formation includes both an inwardly and outwardly depending lip portion relative to the peripheral edge of the body. The mask may accommodate a range of facial dimensions whilst still retaining an effective seal.

14 Claims, 3 Drawing Sheets

(56) References Cited

U.S. PATENT DOCUMENTS

| | | | |
|---|---|---|---|
| 4,907,584 A | | 3/1990 | McGinnis |
| 4,951,664 A | | 8/1990 | Niemeyer |
| 5,673,690 A | * | 10/1997 | Tayebi ............... A41D 13/1115 |
| | | | 128/205.27 |
| 6,615,834 B2 | | 9/2003 | Gradon et al. |
| 6,701,926 B2 | | 3/2004 | Olsen et al. |
| 6,789,541 B2 | | 9/2004 | Olsen et al. |
| 2006/0225740 A1 | | 10/2006 | Eaton et al. |
| 2010/0258131 A1 | | 10/2010 | Gaffney et al. |

FOREIGN PATENT DOCUMENTS

| | | | | |
|---|---|---|---|---|
| EP | 0264772 A1 | | 4/1988 | |
| EP | 0838237 A2 | * | 4/1998 | ............... A62B 9/02 |
| EP | 1258266 A1 | | 11/2002 | |
| EP | 1841481 A1 | | 10/2007 | |
| GB | 848215 | | 9/1960 | |
| GB | 2412594 A | | 10/2005 | |
| GB | 2412594 A | * | 4/2006 | ............ A61M 16/06 |
| WO | 01/62326 A1 | | 8/2001 | |
| WO | 2005/118040 A1 | | 12/2005 | |
| WO | 2006/074513 A1 | | 7/2006 | |
| WO | 2009/022249 A2 | | 2/2009 | |
| WO | 2010/016774 A1 | | 2/2010 | |
| WO | 2012047121 A1 | | 4/2012 | |
| WO | 2013/026091 A1 | | 2/2013 | |
| WO | 2013/108145 A1 | | 7/2013 | |
| WO | 2014/141029 A1 | | 9/2014 | |

OTHER PUBLICATIONS

Search Report for Great Britain Patent Application No. GB1107314.5, dated Jun. 27, 2012 (1 page).

\* cited by examiner

RESPIRATORY MASK

This application is a national stage application under 35 U.S.C. § 371 of PCT International Application No. PCT/GB2012/050676, filed Mar. 27, 2012, which claims the priority of Great Britain Patent Application No. 1107314.5, filed on May 3, 2011.

The present invention relates to respiratory masks suitable for delivery of gas for inhalation by a patient and more particularly, although not exclusively, to a mask which is suitable for use in therapy.

Respiratory masks are used to supply inhalation gases, and possibly also atomised liquids such as drugs in solution, to the airways of a patient. In general, a gas is supplied to a respiratory enclosure defined by the respiratory mask and the face of the patient, and the patient inhales the inhalation gas from this respiratory enclosure. Conventional masks typically also have an inlet for the inhalation gas, and an outlet through which exhaled gas escapes the respiratory mask.

A conventional respiratory mask is relatively flexible, and is typically formed as a unitary component of polyvinylchloride (PVC) material. This unitary component defines a cavity, and typically has an outwardly-turned peripheral rim that is urged against the patient's face, about their nose and mouth, when fitted to the patient.

In order to maintain an effective seal between the peripheral rim of the respiratory mask and the patient's face, conventional respiratory masks have an elasticated strap that is placed about the patient's head so as to urge the respiratory mask against the face of the patient. In addition, a nose clip is typically fitted about the portion of the mask that surrounds the patient's nose so as to further improve the seal between the mask and the patient's face.

Respiratory masks such as those described above may be used for oxygen therapy in which oxygen is administered to a patient at a concentration greater than that of ambient air, and/or aerosol therapy in which a fine mist of a drug in solution is inhaled by a patient.

The relatively flexible PVC material of conventional respiratory masks allows these masks to conform to the contours of a patient's face to a limited degree in order to provide a seal. However the quality of the seal is relatively poor such that air may be entrained around the side of the mask in use. Additionally gas, intended for inhalation, may be leaked around the mask edges. Any such leakage requires the delivery of a larger volume of gas and/or an elevated delivery pressure to a patient. An insufficient seal also leads to uncertainty over the concentration of fluid being inhaled by the patient.

It has therefore been proposed to provide a mask which is formed substantially of a more rigid plastics material but which has a seal about the periphery of the mask which is formed of a more supple material. An example of such a mask is provided in UK Patent Application 2412594, which provides for an improved seal over conventional PVC masks.

In providing an improved seal, it is generally necessary to provide a tighter fit to the patient's face. This can be achieved by tightening a strap which passes around the patient's head during use. However it has been found that a tighter fit to a patient's face generally implies a more limited range of fit that can be accommodated by a mask. As such, a balance needs to be struck between a mask which can accommodate a wide range of face sizes or profiles and a mask which can provide an improved seal.

It is an aim of the present invention to provide a mask which can provide an adequate seal for a relatively large range of face shapes and sizes.

According to the invention, there is provided a respiratory mask for delivering an inhalation gas to the airways of a wearer, the respiratory mask comprising a body of generally concave shape and having a peripheral edge, the body being adapted to provide a cavity in use about the mouth and nose of a wearer such that the inhalation gas can be inhaled by the patient from the cavity, the body having an inlet port that is engageable with a supply of inhalation gas and in communication with the cavity, wherein the respiratory mask includes a resilient seal formation depending from at least a portion of the peripheral edge, the resilient seal formation comprising both an inwardly and outwardly depending lip portion relative to the peripheral edge of the body, the inwardly depending lip portion being arranged in use to pass closely beneath the mandible of a wearer having a relatively smaller facial dimension and the outwardly depending lip portion being arranged to pass closely beneath the mandible of a wearer having a relatively larger facial dimension.

A primary advantage of the invention is that a mask can be provided which beneficially forms a seal beneath the chin or lower jaw of a wearer but which also allows for a relatively larger range of facial profiles to be accommodated by a single mask design. Accordingly, the inwardly depending lip portion provides a seal about the mandible for wearers having a facial dimension such that their nose and lower jaw can be located within the peripheral edge of the mask. The outwardly depending lip portion provides a seal about the mandible for wearers having a facial dimension such that their nose and lower jaw cannot be located within the peripheral edge of the mask (i.e. such that their chin extends beyond the peripheral edge of the mask when the mask is located against the bridge of the wearer's nose).

Thus the mask may be considered to be range-taking in a manner which does not adversely diminish the seal provided about the periphery of the mask. Each of the lip formations may advantageously be considered to be range-taking in its own right for relatively smaller and relatively larger wearer face profiles respectively.

The facial dimension may comprise any, or any combination, of the total facial height, the mid facial height or lower facial height.

The resilient seal formation may be elastomeric. This may serve to improve the seal formed between the mask body and the face of the patient, and may also provide a more comfortable fit for a patient.

The body may be shaped to provide a mandible engaging portion for wearers having a relatively smaller facial dimension. The mandible engaging portion may be arranged to pass closely beneath the mandible of a wearer and may take the form of concave mask portion, which may be shaped so as to provide a sill or shelf formation beneath the wearer's mandible. The sill or shelf portion may be curved. The mandible engaging portion may also have a front facing wall portion which may be arranged for abutment against a wearer's chin. The mandible engaging portion may take the form of a chin cup.

The portion of the body periphery about which the inwardly and outwardly depending lip portions extend may comprise a first or lower mask periphery portion. The seal formation may extend around substantially the entire peripheral edge of the mask body. The inwardly depending lip portion may extend around substantially the entire peripheral edge of the mask body. The outwardly depending lip portion may extend around only a part of the peripheral edge of the body. The outwardly depending lip formation may extend around the first portion. An outwardly depending lip formation may also extend about a second part of the peripheral edge which may be spaced from the first portion and may comprise a nasal contact region.

The mask body may comprise a first material. The mask body may be formed substantially of the first material. The seal formation may be formed substantially of a second material. The first material may display greater rigidity or stiffness than the second material. The second material is preferably resiliently deformable.

The inwardly depending lip portion may be generally planar in form. The inwardly depending lip portion may take the form of a simple upstanding wall which follows the contour of the peripheral edge of the body.

In one embodiment the outwardly depending lip portion may be generally concave or inwardly-turned in shape. The outwardly depending lip portion may be concave in the same sense as the mask body. The outwardly depending lip portion may be shaped so as to provide a sill or shelf formation beneath the wearer's mandible. The outwardly depending lip formation may be shaped in the form of a chin cup. The outwardly depending lip portion may be shaped so as to provide both a forward facing lip portion and also a downward facing lip portion.

The periphery of the body in the vicinity of the inner and outer lip portions may be shaped from a central point or region of the mask by a first radius. The inwardly depending lip portion typically has an inner edge of radius which is smaller than the first radius. The outwardly depending lip portion typically has an outer edge of radius which is larger than the first radius.

According to one embodiment, the inwardly depending lip portion has an inner edge with a radius of curvature in the vicinity of the first periphery portion of the body which is greater than the radius of curvature of an outer edge of the outwardly depending lip portion in the vicinity of the first periphery portion of the body. The inwardly depending lip portion may comprise a substantially flat or linear inner edge portion. The outwardly depending lip portion may comprise an outer edge which displays a substantially constant radius of curvature in the vicinity of the first periphery portion of the body.

In one embodiment, the inwardly and outwardly depending lip portions may be formed as a unitary or continuous member. There may be a smooth transition between the inwardly and outwardly depending lip portions.

The seal formation may be formed by injection moulding. The body and seal formation may be co-formed by way of a moulding process. The body and seal formation may be co-formed as part of a so-called multi-shot injection moulding process such as a two-shot injection moulding process. In particular, the mask body is preferably injection moulded as a single component of a relatively rigid material, and the elastomeric material of the respiratory mask is then preferably injection moulded onto the surface of the mask body. The mask body and the elastomeric parts of the respiratory mask are bonded together by this process.

The outwardly depending lip portion may be considered to provide a resilient extension portion of the mask body depending outwardly from a lower peripheral edge portion thereof.

According to one embodiment, the mask may provide for a first fitment condition in which a wearer's mandible is contained within the peripheral edge of the body. The mask may provide for a second fitment condition in which the wearer's mandible protrudes beyond the peripheral edge of the body. The wearer's mandible may deform the inwardly facing lip portion in the first condition, so that the inwardly depending lip formation is urged against the face of the wearer, thereby forming a seal between the respiratory mask and the face of the wearer. The wearer's chin or mental protuberance may abut against the mask body in the first condition. The wearer's chin or mental protuberance may abut against the outwardly depending lip portion in the second condition.

A relatively rigid mask body preferably defines the shape of the cavity and may be considered to provide an outer cavity wall. By "rigid" mask body is meant that the mask body maintains its shape when subjected to normal handling conditions. The mask body is preferably formed from plastics material in an injection moulding process. Most preferably, the mask body is formed of polypropylene.

The inlet port preferably comprises an opening in the wall of the cavity, and a conventional tubular connector extending outwardly therefrom. Most preferably, the tubular connector extends from an opening in a nose portion of the mask body into a space adjacent to a mouth portion. The respiratory mask body may include openings that allow exhaled gases to escape from the cavity of the respiratory mask, during use. Where the respiratory mask is to be used for delivering a high concentration of an inhalation gas, such as oxygen, to a patient, the openings in the mask body may each include a valve.

The inwardly and/or outwardly depending lip portions may be orientated generally perpendicularly to the wall of the cavity at the periphery of the mask.

The elastomeric material of the respiratory mask is preferably a Styrene-Ethylene-Butylene-Styrene (SEBS)-based thermoplastic elastomer.

The respiratory mask according to the invention may include means for securing the mask to the patient, in use. Such means may include an elasticated cord or strap that is fitted around the patient's head to urge the respiratory mask against the face of the patient. The elasticated cord or strap may be formed of elastomeric material, and may therefore be formed integrally with the remainder of the respiratory mask using the two-shot injection moulding process. Alternatively, the elasticated cord or strap may be formed as a separate component.

A mask according to the present invention may carry the advantage that it may allow the cord or strap to be worn over the ears of a wearer. The mask arrangement according to the invention may help prevent a mask from slipping down and/or rising up a wearer's face in use.

According to a further aspect of the invention, there is provided a respiratory mask for delivering an inhalation gas to the airways of a wearer, the respiratory mask comprising a body of generally concave shape and having a peripheral edge, the body being adapted to provide a cavity in use about the mouth and nose of a wearer, the body having an inlet port that is engageable with a supply of inhalation gas and in communication with the cavity, wherein the respiratory mask includes a resilient seal formation depending from at least a portion of the peripheral edge, the resilient seal formation comprising both an inwardly and outwardly depending lip portion relative to the peripheral edge of the body, the inwardly and outwardly depending lip portions providing for at least first and a second alternative fitment conditions in use.

The first and second fitment conditions may allow the mask to be range-taking with respect to one or more facial dimensions of a wearer. Any optional features described with respect to the first aspect may also be applicable to the further aspect of the invention.

The term 'gas' or 'inhalation gas' or 'inhalation fluid' as used herein is intended to cover gas streams which carry an amount vapour or liquid state matter therein as well as substantially gas-only streams.

The invention will now be described in greater detail, by way of illustration only, with reference to the accompanying drawings, in which.

The respiratory mask according to the invention is advantageous principally because the resilient sealing member improves the seal between the respiratory mask and the face of the patient, and may also allow a single size of mask to be used with faces having a greater range of sizes than has hitherto been possible. The respiratory mask is particularly advantageous when used for oxygen and/or aerosol therapy.

Turning firstly to FIGS. 1 to 4, there is shown a respiratory mask according to the present invention, which is suitable for the delivery of a gas to a wearer, such as a patient. The respiratory mask comprises a mask body 10, formed from a suitably strong and relatively rigid plastics material, such as polypropylene, and a sealing formation 20 formed from a Styrene-Ethylene-Butylene-Styrene (SEBS)-based thermoplastic elastomer.

The respiratory mask is manufactured using a so-called two-shot injection moulding process. In particular, the mask body 10 is firstly injection moulded as a single component, and the sealing formation 20 is then injection moulded onto the surface of the mask body 10. The mask body 10 and the sealing formation 20 are bonded together by this process.

The mask body 10 is generally concave, so as to define a cavity from which an inhalation gas is delivered to a patient, and comprises a mouth portion 11 and a nose portion 12. The mask body is shaped such that the depth of the cavity defined by the nose portion is greater than the depth of the cavity defined by the mouth portion. The nose portion 12 is tapered towards an apex 12A that is shaped to fit around the bridge of the patient's nose.

Figure 11:
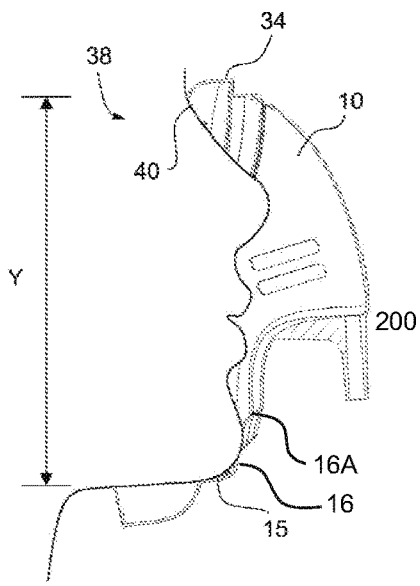

The mouth portion 11 generally comprises a forward-facing, front wall 14 and a laterally-extending bottom wall portion 15, which may otherwise be described as a sill formation. The front wall 14 comprises a step 16A, as shown in FIG. 11, and adjoins the sill 15 at an intermediate wall portion 16, the interior face of which serves as an abutment in use as will be described below. To either side of the front wall 14, there are side wall portions 17, which are arranged to be located adjacent a wearer's cheeks or jowls, and particularly the lower portion thereof, in use.

The sealing formation 20 is a unitary flange member that is bonded to, and extends from, the edge of the mask body 10. The sealing formation 20 comprises an inwardly depending lip portion 22, which extends into the opening defined by the edge of the mask body 10, such that the lip portion 22 forms a substantially flat, and continuous, contact surface within the periphery of the mask that is urged against the face of the patient during use. The sealing lip 22, and hence the contact surface, entirely surrounds the inner edge of the mask body 10.

The elastomeric nature of the sealing formation 20 enables an effective seal to be formed between the contact surface of the respiratory mask and the face of the patient. Also, the lip portion 22 has discontinuities therein in the form of slits 24 which allow the lip portion 22 to deform about the different contour portions of a wearer's face. Such slits 24 are provided in the region of the apex 12A and also in the lip portion where it is intended to contact a wearer's cheeks and/or lower jaw in use.

The lip portion 22 extends in a generally perpendicular direction relative to the mask body 10 at its peripheral edge in the manner of an upstanding wall. The lip portion 22 is of substantially continuous height around the periphery of the mask such that the inner edge of the lip follows the contours of the mask body periphery.

However at the lower wall portion 15 of the mask body, the lip portion 22 is shaped so as to provide an inner edge region 26 which is substantially flat. This allows the lip portion to accommodate a wide range of lower jaw profiles of a wearer. This may also allow a depth of lip which accommodates a relatively wide range of lower face heights or total face heights of potential wearers.

The sealing formation 20 of the respiratory mask according to the invention also comprises an outwardly depending lip formation 28 in the vicinity of the mask body sill 15. The lip portions 22 and 28 are formed integrally as portions of the sealing formation 20. The lip portion 28 extends outwardly from the periphery of the mask body, primarily below the lower edge of the mask body. In other embodiments, the lip portion 28 may also extend outwardly from the sides (i.e. laterally) of the mask body.

Figure 1:
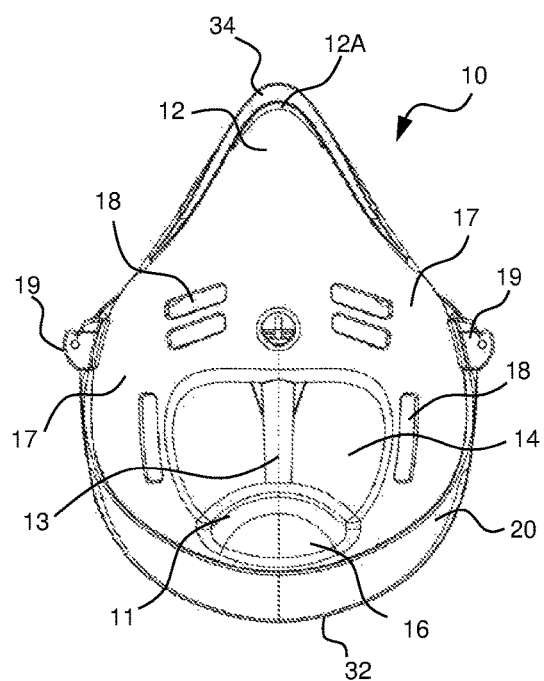
FIG. 1 is a front view of a respiratory mask according to a first embodiment of the invention.
Figure 2:
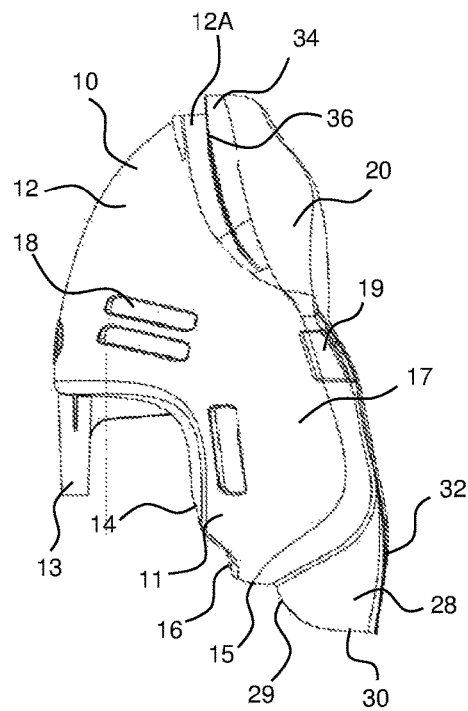
FIG. 2 is a side view of the respiratory mask of FIG. 1.
Figure 3:
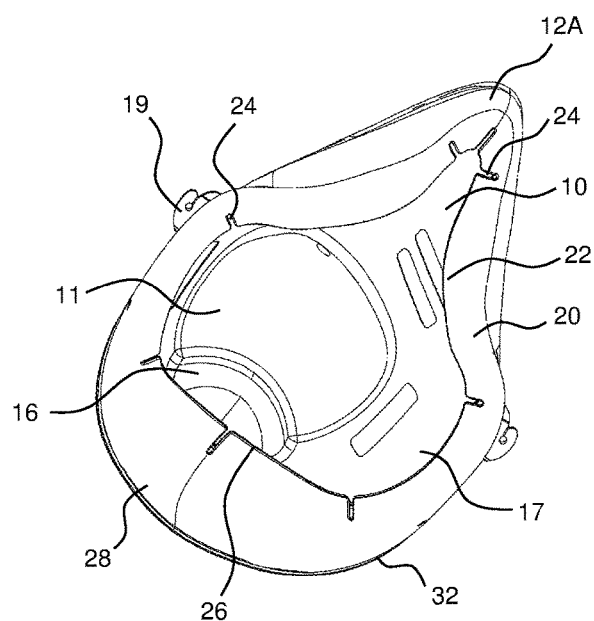
FIG. 3 is a three-dimensional view of the rear of the mask of FIG. 1.
Figure 4:
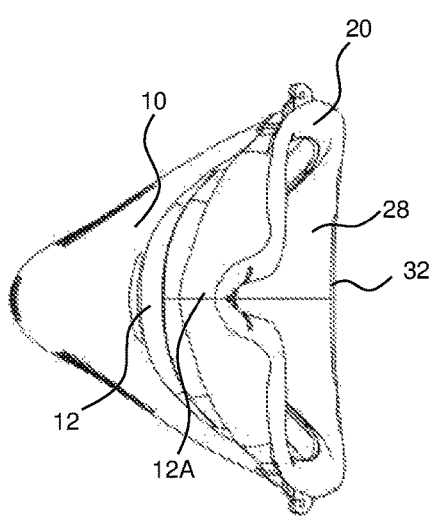
FIG. 4 is an above view of the respiratory mask of FIG. 1.

The lip portion 28 (as can be seen in FIG. 2) is curved in shape so as to provide a generally concave form and has a front facing wall portion 29 and a generally laterally extending, or downward facing, wall portion 30. The lip portion 28 has an outer edge 32 which follows a generally smooth profile of substantially constant curvature in plan, as can be seen in FIGS. 1 and 3. When viewed from above, it can be seen that the outer edge 32 is generally straight, such that the edge is contained substantially within a plane (i.e. a substantially vertical plane in the orientation of FIG. 2).

A further outwardly depending lip portion 34 may be provided at the periphery of the nose region 12 of the mask body 10. That lip portion 34 may be shaped to taper towards an apex in a manner similar to the profile of the mask body 10. The lip portion 34 and/or the associated part of the body periphery may comprise one or more folds or steps 36 (see FIG. 2) so as to provide a cushioning effect and/or close fitment against a wearer's nose.

The lip portions 22 and 34 provide an effective seal between the respiratory mask and the face of the patient, which may allow the respiratory mask to be used without a nose clip.

The mask body 10 further comprises an inlet port 13 for connection to a supply of an inhalation gas, such as oxygen, and a plurality of exhalation openings 18. The inlet port 13 comprises an opening in a lower wall of the nose portion 12, and a tubular connector that extends downwardly (as viewed in FIGS. 1 and 2) from this opening into the space in front of the mouth portion 11. In use, a supply of an inhalation gas is connected to the tubular connector of the inlet port 13 so as to supply the inhalation gas to the cavity of the respiratory mask and hence the airways of the patient.

The exhalation openings 18 in this embodiment are elongate apertures in the wall of the mask body 10 that allow exhaled gases to exit the cavity of the respiratory mask. A pair of exhalation openings is provided to either side of the nose portion 12. A generally vertically aligned exhalation opening is also provided on either side of the font face 14 of the mouth portion 11 (i.e. in side walls 17). Whilst such arrangement of openings has been found to be beneficial, it will be appreciated that other shapes, configurations and orientations are possible.

The body 10 has a pair of outwardly extending flange formations 19 on either side of the respiratory mask which are arranged to receive an elastic strap in use. Each flange is located adjacent the peripheral edge of the mask body and has an aperture, to which an elasticated strap (not shown in the Figures) is attached, in use. The elastic strap extends between the flanges 19, and fits around the patient's head when the respiratory mask is fitted to the patient. In use, the strap is adjusted so that the respiratory mask is urged against the face of the patient with an appropriate force to ensure that an effective seal is formed between the periphery of the respiratory mask and the wearer's face, without causing excessive discomfort for the wearer.

Figure 10:
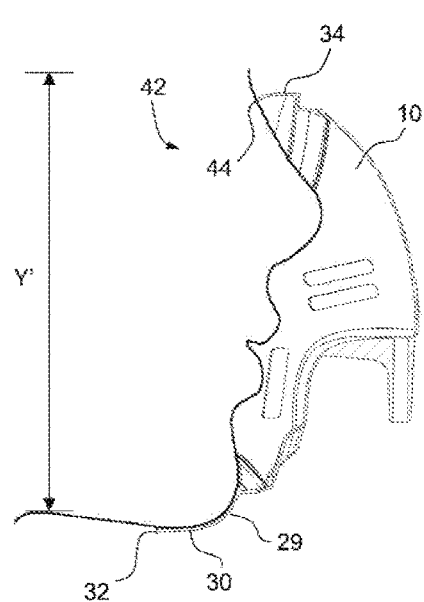
FIG. 10 shows a section view of the mask of FIG. 1 in a second usage condition; and, FIG. 11 shows a section view of the mask of FIG. 1 in a first usage condition.

The mask of FIG. 1 is shown in different usage conditions in FIGS. 10 and 11. For use, the mask is located against a wearer's face. The correct positioning of the mask is generally determined by the location of the apex 12A of the nose portion 12 against the bridge of a wearer's nose. This is typically at, or slightly below, the nasion. The inwardly depending lip portion 22 contacts the wearer's face about the periphery of the mask such that the wearer's nose and mouth are located in the mask cavity. The wearer's mouth is accommodated within the mouth portion 11 of the mask body 10 and the wearer's nose is accommodated within the nose portion 12 of the mask body 10. The nose portion 12 of the mask body 10 is tapered towards the upper end of the mask and hence the bridge of the patient's nose.

However the total facial height of wearers (i.e. the height from the wearer's nasion to the gnathion, or lowest point of the mandible) can vary significantly between wearers. Accordingly, when apex 12A of the mask is correctly positioned, the wearer's face, particularly their lower jaw or chin, may engage with the lower portion of the mask at varying locations. For conventional masks, this varying fitment can adversely affect the quality of the seal provided between the mask and face. This problem is addressed by the mask according to the invention as will be described in relation to FIGS. 10 and 11 below.

In FIG. 11, the mask is fitted to a wearer's face 38, the facial length of which is indicated as dimension Y. In this example, the facial length is relatively small, such that, when the apex of the sealing lip portion 34 is located against the bridge 40 of the wearer's nose, the lowermost lateral face, or sill 15, of the mask body 10 can be located immediately beneath the wearer's mandible, more specifically beneath the wearer's gnathion or mental protuberance. The frontal portion of the wearer's chin thus abuts against the front wall portion 16 of the mask body 10. In this condition, the inwardly depending lip portion 22, and particularly inner edge 26 thereof, is contacted by the wearer's mandible such that it is deformed in a direction towards the mask body, or otherwise into the mask cavity.

Thus the mask body provides a chin cup formation and the inner lip portion 22 provides a seal against the wearer's lower jaw.

In FIG. 10, the mask is fitted to a wearer's face 42, having a relatively large facial length, which is indicated as dimension Y'. When the apex of the sealing lip portion 34 is located against the bridge 44 of this wearer's nose, the wearer's gnathion or lower jaw protrudes beyond the lowermost lateral face, or sill 15, of the mask body 10, even when the wearer's jaw is closed. Accordingly, in this condition, the frontal portion of the wearer's chin abuts against the front wall portion 29 of outwardly protruding lip portion 28 and the lower region of the wearer's mandible contacts the sill 30 of the lip portion 28. In this condition, the seal with the wearer's mandible is provided primarily by the lip portion 28, which serves as a chin cup. The inwardly depending lip portion 22 may also contact the front of the wearer's chin to provide a further sealing effect.

Accordingly the mask provides a good seal against the wearer's face in either of the conditions of FIGS. 10 and 11 such that the wearer can inhale and exhale with minimal loss of gas around the peripheral edge of the mask.

It is further noted as an advantage of the present invention that, in providing for different facial lengths of wearers, the mask may also allow for movement of a wearer's jaw without substantial loss of the seal between the mask and the wearer's face, such as for example, when a wearer is talking, yawning, masticating or the like. In this regard, the resilient and flexible nature of the lip portion 28 can accommodate a degree of jaw movement.

Also, when the outwardly depending lip portion is redundant, such as when the mask is worn in the first condition as shown in FIG. 11, it is possible that the outwardly depending lip portion can be turned or flipped over onto the outer faces 15 and 16 of the mask body 10. Thus the lip portion 28 can be actuated between an in-use and a storage condition and vice versa.

Turning now to FIGS. 5-9, further embodiments of the invention are shown. Each of those embodiments share the same physical features and associated method of fitment or operation to the embodiments described above, save for the differences described below. Accordingly, like features between the embodiments will not be reiterated for conciseness. Whilst the embodiment of FIGS. 1-4 is suited for attachment to a conventional gas delivery system for the supply of a gas, such as oxygen, to a patient, it is not limited to such use and the mask may be substituted for any of the embodiments described below wherever practicable.

Figure 5:
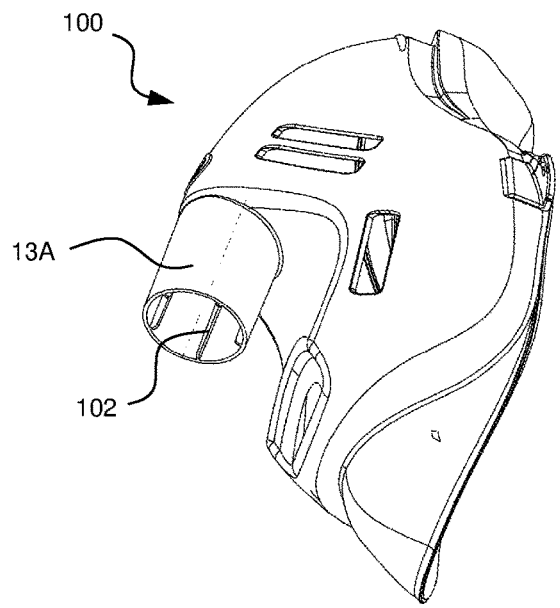
FIG. 5 is a three-dimensional view from below a mask according to a second embodiment of the invention.
Figure 6:
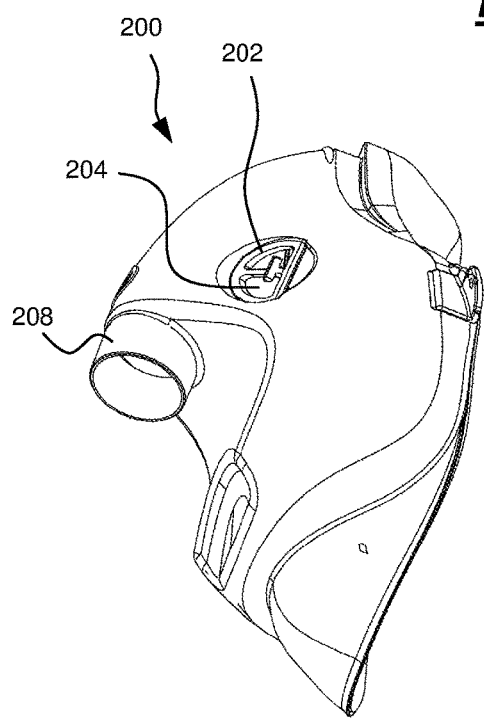
FIG. 6 is a three-dimensional view from below of a respiratory mask according to a third embodiment of the invention.

The mask of FIG. 5 is equivalent to that of FIG. 1, save that the inlet port 13A has a greater width or diameter than the corresponding port 13 in FIGS. 1-4. The inlet port 13A also comprises a plurality of location formations in the form of ribs or splines 102 spaced about its inner surface. The splines are elongate in form and aligned with an axis of the inlet port. The inlet port 13A is thus arranged to receive a corresponding duct (not shown) within its interior. Such an arrangement is particularly suitable to provide a connection with ducting as may be used for delivery of an atomised liquid or vapour to a wearer, such as for example by way of an aerosol, and accordingly, mask 100 may be used as an aerosol therapy mask.

The mask 200 of FIGS. 6-9 may be suitable for use as a high-concentration delivery mask, wherein gas is communicated to a wearer in a pre-determined concentration, which is desired to be closely maintained. Accordingly, the openings 18 of mask body 10 have been substituted in mask 200 for openings 202, which have an associated closure member 204. The mask body of mask 200 is shaped to provide a support structure 206 across the openings 202 so as to hold the closure member in place over the opening. The openings 202 and associated closure members are generally circular in plan in this embodiment.

Figure 9:
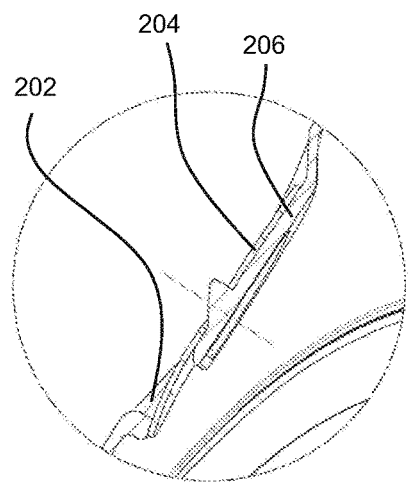
FIG. 9 shows detail of the valve of FIG. 8 through section A-A.

As can be seen in FIG. 9, the closure 204 is resiliently deformable and is tucked under an edge of the opening in the mask body such that the closure 204 is biased towards a closed position. Accordingly the closure only opens to allow fluid communication with the exterior of the mask body upon application of a pressure differential there-across which is sufficient to overcome the resilience of the closure member material.

In the manner described above, the openings 202 and associated closure members 204 act as valves to control discharge of fluid from the mask during exhalation by the wearer. Accordingly the interior of the mask is generally sealed from the exterior of the mask so as to allow greater control and predictability of the fluid inhaled by the wearer. This is particularly suited to high-concentration therapy applications.

Figure 7:
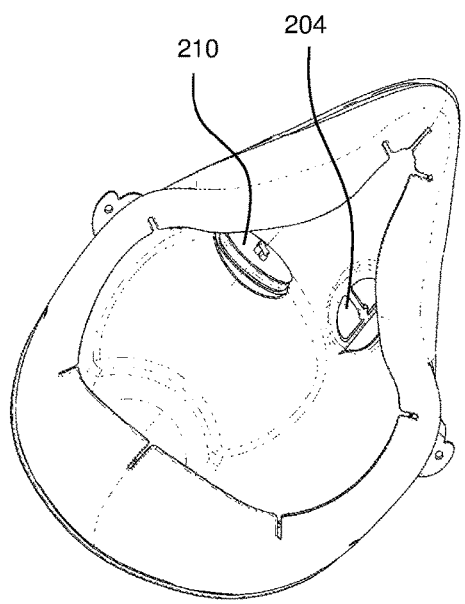
FIG. 7 is a three-dimensional view of the rear of the mask of FIG. 6.
Figure 8:
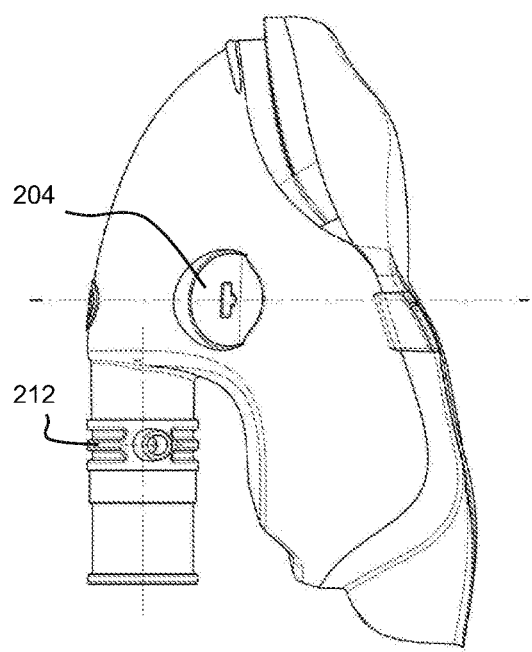
FIG. 8 is a side view of an assembly comprising the mask of FIG. 6.

In FIG. 7, it can be seen that a similar valve configuration 210 is provided at the inlet port 208 to regulate flow into the mask during inspiration. That valve may be formed in the mask body itself but is typically provided within an associated ducting 212 which is connected to the inlet duct 208 for use as shown in FIG. 8. The ducting 212 may be of conventional design and the inlet port 208 may be shaped to accommodate such ducting. In particular the inlet port 208 may be of relatively short length and increased diameter compared to the inlet port of FIG. 1. Where the respiratory mask is to be used for delivering a high concentration of an inhalation gas, such as oxygen, to a patient, the openings in a reservoir bag will generally be connected to the inlet port via associated ducting.

All the embodiments described above display corresponding peripheral sealing formations and thus can be fitted to wearers in the manner described above in relation to FIGS. 1-4, 10 and 11.

The invention claimed is:

1. A respiratory mask for delivering an inhalation fluid to the airways of a wearer, the respiratory mask comprising:
   a body of generally concave shape and having a peripheral edge, the body comprising a mouth portion and a nose portion adapted to provide a cavity in use about the mouth and nose of the wearer such that the inhalation fluid can be inhaled by the wearer from the cavity, wherein the depth of the cavity defined by the nose portion is greater than the depth of the cavity defined by the mouth portion, the body having an inlet port that is engageable with a supply of inhalation fluid and in communication with the cavity; and,
   a resilient seal formation depending from at least a portion of the peripheral edge, the resilient seal formation comprising both a first and a second lip portion relative to the peripheral edge of the body, the first lip portion depending inwardly from the peripheral edge of the body into the cavity and extending entirely around the peripheral edge, the peripheral edge being between the first lip portion and the body, and being arranged to pass closely beneath the mandible of a first wearer having a first facial dimension, such that the first wearer's nose and lower jaw can be simultaneously located within the peripheral edge of the mask, to thereby provide a first fitment condition for the first wearer, the second lip portion depending outwardly from the peripheral edge of the body and being arranged to pass closely beneath the mandible of a second wearer having a second facial dimension relatively larger than the first facial dimension of the first wearer, such that the second wearer's nose and lower jaw cannot be simultaneously located within the peripheral edge of the body, and the second lip portion being concave in shape in the same way as the body so as to provide a chin cup for the second wearer having the second facial dimension, to thereby provide a second fitment condition for the second wearer, and the mouth portion comprising a forward-facing front wall, and a laterally-extending sill formation, the front wall comprising a step extending laterally from an intermediate wall portion of the front wall, the front wall adjoining the sill formation at the intermediate wall portion, wherein the sill formation is arranged to pass beneath the first wearer's mandible and an interior face of the intermediate wall portion provides an upstanding wall surface of the front wall for abutment against a frontal portion of said first wearer's chin.

2. The respiratory mask according to claim 1, wherein the second lip portion depends from only a first region of the peripheral edge of the body.

3. The respiratory mask according to claim 1, wherein the body is formed substantially of a first material and the resilient seal formation is formed substantially of a second material, wherein the rigidity of the first material is greater than that of the second material.

4. The respiratory mask according to claim 1, wherein the resilient seal formation is elastomeric.

5. The respiratory mask according to claim 1, wherein the first and second lip portions are formed as a unitary seal formation.

6. The respiratory mask according to claim 1, wherein the body and the seal formation are formed by a multi-shot moulding process.

7. The respiratory mask according to claim 1, wherein the first lip portion is deformable by the first wearer's mandible in the first fitment condition, so that the first lip portion is urged against the first wearer's face during use, thereby forming a seal between the respiratory mask and the first wearer's face.

8. The respiratory mask according to claim 1, wherein the first facial dimension and the second facial dimension comprise any of the total facial height, the mid facial height or lower facial height of the first wearer and the second wearer.

9. The respiratory mask of claim 1, wherein the first lip portion has discontinuities therein that allow the first lip portion to deform.

10. The respiratory mask of claim 9, wherein the discontinuities are in the form of slits.

11. A respiratory mask for delivering an inhalation fluid to the airways of a wearer, the respiratory mask comprising:
   a body of generally concave shape and having a peripheral edge, the body having a mouth portion and a nose portion adapted to provide a cavity in use about the mouth and nose of the wearer such that the inhalation fluid can be inhaled by the wearer from the cavity, the body having an inlet port that is engageable with a supply of inhalation fluid and in communication with the cavity; and a resilient seal formation depending from at least a portion of the peripheral edge of the body, the resilient seal formation comprising both an inwardly and outwardly depending lip portion relative to the peripheral edge of the body, the inwardly depending lip portion depending into the cavity and being arranged to pass closely beneath the mandible of a first wearer having a first facial dimension, such that the first wearer's nose and lower jaw can be simultaneously located within the peripheral edge of the mask, to thereby provide a first fitment condition for the first wearer, the outwardly depending lip portion being arranged to pass closely beneath the mandible of a second wearer having a second facial dimension relatively larger than the first facial dimension of the first wearer, such that the second wearer's nose and lower jaw cannot be simultaneously located within the peripheral edge of the body, to thereby provide a second fitment condition for the second wearer, wherein the inwardly depending lip portion extends around the entire peripheral edge of the mask body, the peripheral edge being between the inwardly depending lip portion and the body, and the mouth portion comprising a forward-facing front wall, and a laterally-extending sill formation, the front wall comprising a step extending laterally from an intermediate wall portion of the front wall, the front wall adjoining the sill formation at the intermediate wall portion, wherein the sill formation is arranged to pass beneath the first wearer's mandible and an interior face of the intermediate wall portion provides an upstanding wall surface of the front wall for abutment against a frontal portion of said first wearer's chin.

12. The respiratory mask of claim 11, wherein the inwardly depending lip portion has discontinuities therein which allow the inwardly depending lip portion to deform.

13. The respiratory mask of claim 12, wherein the discontinuities are in the form of slits.

14. A respiratory mask for delivering an inhalation fluid to the airways of a wearer, the respiratory mask comprising:

a body of generally concave shape and having a peripheral edge, the body having a mouth portion and a nose portion adapted to provide a cavity in use about both the mouth and nose of the wearer such that the inhalation fluid can be inhaled by the wearer from the cavity, wherein the depth of the cavity defined by the nose portion is greater than the depth of the cavity defined by the mouth portion, the body having an inlet port that is engageable with a supply of inhalation gas and in communication with the cavity;

a resilient seal formation depending from at least a portion of the peripheral edge, the resilient seal formation comprising both a first and a second lip portion relative to the peripheral edge of the body, the first lip portion depending inwardly from the peripheral edge of the body into the cavity and being arranged to pass closely beneath the mandible of a first wearer having a first facial dimension such that the first wearer's nose and lower jaw can be simultaneously located within the peripheral edge of the mask, the second lip portion depending outwardly from the peripheral edge of the body and being arranged to pass closely beneath the mandible of a second wearer having a second facial dimension, relatively larger than the first facial dimension of the first wearer such that the second wearer's nose and lower jaw cannot be simultaneously located within the peripheral edge of the mask, and the mouth portion comprising a forward-facing front wall, and a laterally-extending sill formation, the front wall comprising a step extending laterally from an intermediate wall portion of the front wall and, the front wall adjoining the sill formation at the intermediate wall portion, wherein the sill formation is arranged to pass beneath the first wearer's mandible and an interior face of the intermediate wall portion provides an upstanding wall surface of the front wall for abutment against a frontal portion of said first wearer's chin.

\* \* \* \* \*